United States Patent
Allen, Jr.

(10) Patent No.: US 6,567,693 B1
(45) Date of Patent: *May 20, 2003

(54) IONTOPHORETIC TRANSDERMAL DELIVERY DEVICE

(75) Inventor: Loyd V. Allen, Jr., Edmond, OK (US)

(73) Assignee: The Board of Regents of the University of Oklahoma

(*) Notice: Subject to any disclaimer, the term of this patent is extended or adjusted under 35 U.S.C. 154(b) by 335 days.

This patent is subject to a terminal disclaimer.

(21) Appl. No.: 09/594,320

(22) Filed: Jun. 15, 2000

Related U.S. Application Data

(63) Continuation of application No. 09/047,296, filed on Mar. 24, 1998, now Pat. No. 6,119,036.
(60) Provisional application No. 60/041,614, filed on Mar. 26, 1997.

(51) Int. Cl.[7] .................................................. A61N 1/30
(52) U.S. Cl. ........................................ 604/20; 424/449
(58) Field of Search ....................... 604/20, 289, 112, 604/172, 304; 424/448, 449

(56) References Cited

U.S. PATENT DOCUMENTS

| | | | |
|---|---|---|---|
| 4,622,031 A | 11/1986 | Sibalis ........................ 604/20 |
| 4,690,683 A | 9/1987 | Chien et al. ............ 424/449 X |
| 4,725,263 A | 2/1988 | McNichols et al. ........... 604/20 |
| 4,820,263 A | 4/1989 | Spevak et al. ................. 604/20 |
| 5,057,072 A | 10/1991 | Phipps ......................... 604/20 |
| 5,084,008 A | 1/1992 | Phipps ......................... 604/20 |
| 5,087,241 A | 2/1992 | Mathiesen et al. ............ 604/20 |
| 5,162,042 A | 11/1992 | Gyory et al. .................. 604/20 |
| 5,203,768 A | 4/1993 | Haak et al. .................... 604/20 |
| 5,221,254 A | 6/1993 | Phipps ......................... 604/20 |
| 5,254,346 A | 10/1993 | Tucker et al. ............ 424/449 X |
| 5,284,471 A | 2/1994 | Sage, Jr. ........................ 604/20 |
| 5,320,731 A | 6/1994 | Muller et al. ........... 204/299 R |
| 5,322,502 A | 6/1994 | Theeuwes et al. ............. 604/20 |
| 5,334,138 A | 8/1994 | Sage, Jr. et al. ............... 604/20 |
| 5,374,241 A | 12/1994 | Lloyd et al. ................... 604/20 |
| 5,395,310 A | 3/1995 | Untereker et al. ............. 604/20 |
| 5,423,739 A | 6/1995 | Phipps et al. ................. 604/20 |
| 5,445,607 A | 8/1995 | Venkateshwaran et al. ... 604/20 |
| 5,458,569 A | 10/1995 | Kirk, III et al. ............... 604/20 |
| 5,464,387 A | 11/1995 | Haak et al. .................... 604/20 |
| 5,647,844 A | 7/1997 | Haak et al. .................... 604/20 |
| 5,697,896 A | 12/1997 | McNichols et al. ........... 604/20 |
| 5,736,580 A | * 4/1998 | Huntington et al. ......... 514/772 |
| 5,817,004 A | 10/1998 | Evers et al. ................... 604/20 |
| 5,840,336 A | * 11/1998 | Hsu et al. .................... 424/449 |
| 5,882,677 A | 3/1999 | Kupperblatt ................ 424/449 |
| 6,119,036 A | * 9/2000 | Allen, Jr. ..................... 604/20 |

FOREIGN PATENT DOCUMENTS

EP      0278473      8/1988

\* cited by examiner

*Primary Examiner*—Anhtuan T. Nguyen
(74) *Attorney, Agent, or Firm*—Dunlap, Codding, & Rogers, P.C.

(57) ABSTRACT

A conducting silicone matrix incorporating a suspension of a drug in ionized and non-ionized phases in an emulsion of a hydrophobic polymer. In one version, the drug is prepared as a concentrated aqueous suspension incorporated in a silicone matrix with a silicone surfactant. An electrolyte may be incorporated into the silicone matrix for increasing its conductivity. When a current is applied, the drug in individual globules in the drug suspension migrates away from the electrode and becomes concentrated at the distal side of the globules eventually resulting in an increase in the drug concentration distal to the electrode and adjacent to the skin and thereby resulting in transfer of the active drug through the skin. This system provides a matrix with minimal electroendosmotic flow that is current efficient and provides a drug reservoir that can last for several days during application of the drug.

17 Claims, 1 Drawing Sheet

IONTOPHORETIC TRANSDERMAL DELIVERY DEVICE

CROSS-REFERENCE TO RELATED APPLICATIONS

This application is a continuation of application Ser. No. 09/047,296 filed Mar. 24, 1998 now U.S. Pat. No. 6,119,036 claims the benefit of U.S. Provisional Application Serial No. 60/041,614, filed Mar. 26, 1997.

FEDERALLY SPONSORED RESEARCH OR DEVELOPMENT

Not Applicable

BACKGROUND OF THE INVENTION

Transdermal administration of drugs is increasing in popularity. Most transdermal systems deliver the drug by passive diffusion using the concentration gradient as the driving force. Facilitated transdermal systems are also available and include penetration enhancers, phonophoresis and iontophoresis. Most transdermal systems use the non-ionized form of the drug with the exception of iontophoresis, which uses the ionized form. Upon application of a small electric current and the placement of the charged drug under the appropriate electrode, the drug is "repelled" away from the electrode through the skin.

There are four problems typically associated with drug delivery via iontophoresis. First, as the current is applied, electroendosmotic (EEO) flow occurs wherein water moves from the drug-containing matrix into the skin. This osmotic flow carries drug with it but also causes water to accumulate in the interface of the patch and the skin, and limits the time the patch is usable. Second, an ionized drug in aqueous solution is not as stable as one in a non-aqueous system and tends to degrade more rapidly. Most of the patch matrices currently in use include the drug in a hydrophilic "gel", which contains a significant percentage of water. A third problem is that such gels tend to dry out with time, rendering the patch ineffective. Fourth, most iontophoretic patches last for only a few hours under active usage. In most iontophoretic transdermal delivery systems the drug is placed in a solution which is placed on a gauze pad or instilled into a special electrode-containing reservoir with a gel barrier or is incorporated into a water-based hydrogel. An iontophoretic system which employed a drug matrix which avoided most of these problems would be desirable.

DESCRIPTION OF THE PREFERRED EMBODIMENTS

Figure 1:
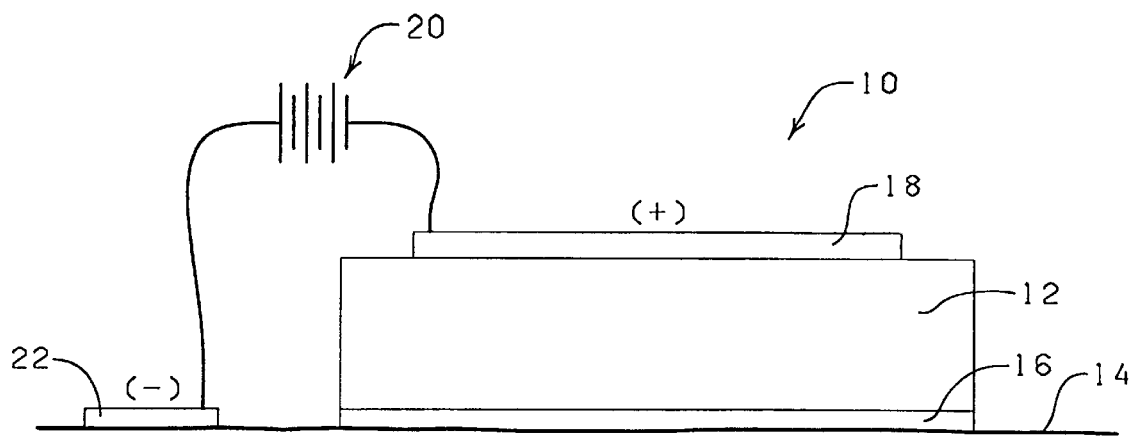
FIG. 1 shows a side view of a delivery device as contemplated herein.

The system described herein comprises a drug-reservoir that provides a ready-to-use, current-efficient, convenient and stable matrix for iontophoretic drug delivery using hydrophobic materials. This system will minimize EEO, enhance the stability of the drug and virtually eliminate the loss of water upon storage. Also, this patch matrix is capable of delivering the drug over a period of several days.

More particularly, the present invention comprises a conducting silicone matrix into which is incorporated a solution suspension of an active drug thereby forming an "aqueous suspension-in-silicone" emulsion. The drug is prepared as a concentrated suspension (which minimizes the degradation rate of the drug) in a water-cosolvent system and is incorporated in a silicone matrix using a silicone surfactant. An electrolyte may be incorporated into the silicone for increasing its conductivity.

When a current is applied to the emulsion matrix, the active drug in the individual aqueous "globules" migrates in a direction away from the active electrode and becomes concentrated at the distal side of the globules. The drug suspension may be buffered at a pH to control the concentration of drug which is in the ionized form. At the drug globule:silicone interface, within the emulsion the un-ionized portion of the drug, and possibly some of the ionized, migrates through the matrix into an adjacent aqueous globule increasing the concentration of drug therein. In adjacent globules, with the applied current, the drug moves away from the electrode causing higher concentrations to build up on the distal sides of the globules in a repeating process. The increase in drug content distal to the electrode and adjacent to the skin results in transfer of the drug through the skin. Because of the low water content, this system provides a matrix with minimal EEO flow resulting in a more efficient use of current and which can maintain active drug delivery for several days.

As contemplated herein, the claimed invention is a transdermal agent delivery device which comprises a matrix comprising a hydrophobic polymer. The matrix is substantially free of a hydrophilic polymer. The hydrophobic polymer may be ionized by an ionizing agent. The polymer is preferably a silicone polymer. Specific examples of silicone polymers which may be used are biocompatible silicone elastomers, for example, those commercially available from Dow Corning including Silastic MDX4-4210, Q7-4510, Q7-2150, and Q7-2146. Other polymers which may comprise the matrix include, but are not limited to, viscous forms of natural and synthetic rubbers such as polybutylene, polyisobutylene, polybutadiene, polyethylene, styrenebutadiene, copolymers, polyisoprene, polyurethane, ethylene/propylene copolymers, polyalkylacrylate polymers, copolyesters, ethylene/acrylic copolymers, and butadiene/acrylonitride copolymers, for example and other polymers such as ethylene vinylacetate (EVA) polymers.

The matrix further preferably comprises a surfactant, for example, Tween 20, Neodol 91-6, Tergitol 15-S-7, Pluronic Poloxamer F68 or F127, Duponol C, Duponol XL. Examples of silicone surfactants are Dow Corning 193 and 190.

Some active transdermal drug delivery systems used in the past have relied on a matrix having a hydrophobic polymer matrix for delivering a drug but these have also included a hydrophilic polymer as a substantial component of the active agent matrix (e.g. U.S. Pat. No. 5,203,768, col. 9, lines 10–20). In the present invention the active agent matrix is substantially free of a hydrophilic polymer. In fact, prior to the present invention it has generally been taught that hydrophobic polymers do not allow the transport of ions therethrough (U.S. Pat. No. 5,203,768, Col. 7, lines 18–22) and therefore the use of hydrophobic polymer matrices have been avoided in iontophoretic drug delivery systems. In a preferred embodiment of the present invention, the conducting matrix comprises a conducting silicone matrix which comprises a silicone polymer which, in a preferred embodiment, has been ionized and therefore rendered conductive by the addition of an electrolyte such as KI. Other suitable electrolytic ionizing substances will readily come to mind to one of ordinary skill in the art; these include NaI, LiI, CaCl$_2$, KCl, NaCl, and LiCl. Alternatively, the conductance may be provided by the drug itself. The silicone matrix preferably further comprises a silicone surfactant which functions to maintain the aqueous drug component (active agent) as a suspension within the silicone matrix. The drug component which is added to the silicone matrix generally comprises a saturated aqueous solution/suspension of the drug. The drug exists as mixed dissolved ionized: suspended non-ionized phases in the suspension. When the aqueous drug suspension is introduced into the silicone matrix, the surfactant within the matrix maintains the drug suspension as an emulsion of droplets or globules. Each globule comprises both ionized and non-ionized forms of the drug. Because the drug is suspended within such globules in the silicone matrix, the quantity of water necessary to maintain the drug in suspension is greatly reduced. For example, in the present system the total water content may be from as low as 1% to 45%, by weight while in a typical gel iontophoresis system water may constitute 90% of the weight of the system. As noted above this is advantageous because it extends the shelf-life and useful life of the iontophoresis system.

While the invention is described herein in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus the following examples, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

In a preferred embodiment, the drug matrix is contained within a patch having a biocompatible permeable pressure sensitive adhesive layer such as Bio-PSA from Dow Corning on one surface (or the adhesive may form part of the matrix) and an active electrode applied to the opposite surface. Other examples of biocompatible adhesives will be readily apparent to those of ordinary skill in the art. The active electrode is connected to a current source such as a battery which is in turn connected to a passive electrode. In use, the drug matrix is attached to a surface of a subject's skin via the adhesive layer (or via an adhesive within the matrix). The passive electrode is attached to an adjacent portion of the skin. As current flows from the active electrode in a direction toward the skin, the ionized drug is driven away from the active electrode toward the skin where its concentration increases, thereby driving it across the patch/skin interface into the skin. As the ionized drug is transferred from the patch to the skin, more non-ionized drug is converted to the mobile, ionized form. The non-ionized drug thereby serves as a drug reservoir which is depleted by slow conversion of non-mobile drug to mobile drug as current is applied to the patch.

Although silicone is the preferred polymer for use as the matrix component of the system, any silicone-like polymer which can be ionized may be employed in the present system, as long as the polymer is inert, can be ionized and is capable of maintaining an aqueous suspension of the drug.

In a preferred embodiment, the matrix comprises, by weight, from 13–18% of a silastic polymeric component, 37–42% of a biocompatible pressure sensitive adhesive (PSA), and 40–50% of a surfactant. Generally the polymeric component comprises less than 25%, the adhesive from 30% to 55%, and the surfactant from 25 to 55%, although it will be understood by a person of ordinary skill in the art that any combination of polymer, adhesive and surfactant may be used as long as the matrix functions in accordance with the present invention.

Specific examples of matrix formulations are:

|  | 1 | 2 | 3 |
|---|---|---|---|
| Silastic Polymer | 14% | 16% | 18% |
| PSA | 40% | 45% | 50% |
| Surfactant | 46% | 39% | 32% |

In a preferred embodiment, the drug/matrix mixture is prepared by mixing drug, alcohol, water and surfactant components. The silastic polymeric component is then added and mixed, followed by the pressure sensitive adhesive. The mixture may then be centrifuged to remove entrapped air. The mixture is mixed again, then poured into a mold and cured at a predetermined temperature for a predetermined time, for example, 37° C. for 24 hours thereby forming, preferably, a solid gel. The weight of the matrix component of the device is preferably 10–12 gm, but is typically from 1–25 gm in typical embodiments, depending on the anticipated use and drug to be delivered.

Shown in FIG. 1 and referred to by the general reference numeral 10 is an example of an active agent delivery system as contemplated herein. The delivery system 10 comprises a drug matrix 12 comprising an ionized hydrophobic polymer and a suspension of an active agent such as a drug. The drug matrix is either placed directly onto a body surface 14 or may be attached thereto by an adhesive layer 16 as discussed above. The adhesive may comprise a discrete layer applied to the matrix or may be present as a mixed component of the matrix, as described elsewhere herein. An active electrode 18 is attached to a portion of the matrix 12 which is opposite the portion of the matrix 12 which is placed against the body surface 14. A current source 20 supplies current to the active electrode 18 and is grounded by a counter electrode 22 which is attached to an adjacent portion of the body surface 14. When the current source 20 is activated current flows from electrode 18 into the matrix 12 and drives active drug toward and into the body surface 14.

Figure 2:
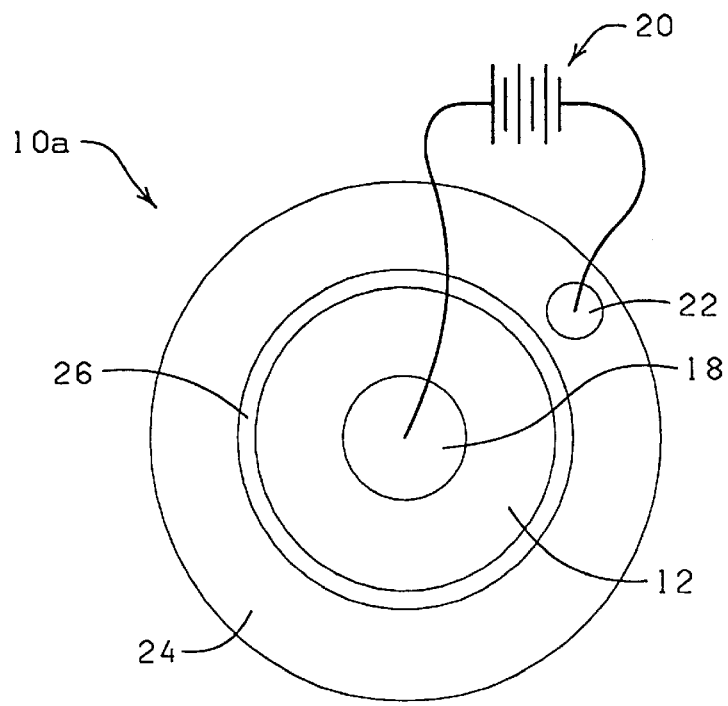
FIG. 2 shows a top plan view of an alternate version of a delivery device.

Shown in FIG. 2 and referred to therein by the general reference numeral 10a is a version of another transdermal delivery device as contemplated herein. The device 10a has a circular configuration and comprises an active matrix portion 12 and a passive matrix portion 24 which is located adjacent the active matrix portion 12 but which is electrically separated therefrom by an insulating layer 26. An active electrode 18 which is disposed upon the active matrix 12 is connected via a current source 20 to a counter electrode 22 which is attached to the passive matrix 24, thereby completing an electric circuit where the device is placed upon a body surface.

Other embodiments of the actual construction of the drug delivery system will be readily apparent to one of ordinary skill in the art, as long as the matrix polymer comprises substantially only a hydrophobic polymer.

Electrodes 18 and 22 are electrically conductive and may be formed of a metal, e.g., a metal foil or metal deposited or painted on a suitable backing. Examples of suitable metals include silver, zinc, silver/silver chloride, aluminum, platinum, stainless steel, gold and titanium. Alternatively, the electrodes 18 and 22 may be formed of a hydrophobic polymer matrix containing a conductive filler such as a metal powder, powdered graphite, carbon fibers or other known electrically conductive filler material.

Electrodes 18 and 22 are electrically connected to the power source 20 using well known means, e.g., printed flexible circuits, metal foils, wires, electrically conductive adhesives or by direct contact. As an alternative to a battery as the power source, the device can be powered by a galvanic couple formed by the donor electrode 18 and counter electrode 22 being composed of dissimilar electrochemical couples and being placed in electrical contact with one another. Typical galvanic couple materials for delivering a cationic agent include a zinc donor electrode 18 and a silver/silver chloride counter electrode 22.

The device may contain electrical circuitry for controlling the level of current produced by device 20. The control circuit may take the form of an on-off switch for "on-demand" drug delivery (e.g., patient controlled delivery of an analgesic for pain relief), a timer, a fixed or variable electrical resistor, a controller which automatically turns the device on and off at some desired periodicity to match the natural or circadian patterns of the body, or other more sophisticated electronic control devices known in the art. For example, it may be desirable to deliver a predetermined constant level of current from device 20 since a constant current level ensures that the active agent is delivered through the skin at a constant rate. The current level can be controlled by a variety of known means, for example, a resistor or a simple circuit that employs a resistor and a field effect transistor. The control circuit may also include an integrated circuit which could be designed to control the dosage of active agent, or even to respond to sensor signals in order to regulate the dosage to maintain a predetermined dosage regimen. A relatively simple circuit can control the current as a function of time, and if desired, generate complex current waveforms such as pulses or sinusoidal waves. In addition, the control circuit may employ a biofeedback system which monitors a biosignal, provides an assessment of the therapy, and adjusts the active agent delivery accordingly. A typical example is the monitoring of the blood sugar level for controlled administration of insulin to a diabetic patient.

Where used herein the term "active agent" refers to therapeutically active substances which are preferably in the form of charged ions and which are able to be delivered through a body surface by iontophoresis at therapeutically effective rates. As used herein, the expressions "agent" and "drug" are used interchangeably and are intended to have their broadest interpretation as any therapeutically active substance which is delivered to a living organism to produce a desired, beneficial, effect. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, cardiostimulants such as dobutamine, antipruritics, antipsychotics, antipyretics, antispasmodics, including gastrointestinal and urinary, anticholinergics, sympathomimetics, xanthine derivatives, cardiovascular preparations including calcium channel blockers such as nifedipine, beta-blockers, beta-agonists such as salbutamol and ritodrine, antiarrythmics, antihypertensives such as atenolol, ACE inhibitors, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetics, prostaglandins, psychostimulants, sedatives and tranquilizers. The invention is also useful in the active delivery of peptides, polypeptides, proteins and other macromolecules.

In use, the active agent delivery system, which has a drug or other active agent disposed within the polymer matrix, is attached to a body surface (e.g., skin) of a human or an animal. As used herein the term "body surface" can also refer to the surface of a plant. When the current source is activated, the charged drug or agent is delivered through the adhesive layer (if present) into the skin (or other body surface). The matrix may also comprise non-charged agents which are delivered into the skin via passive diffusion.

In addition to the drug, the matrix 12 may also contain other materials such as penetration enhancers, dyes, pigments, inert fillers, excipients, and conventional components of pharmaceutical products or transdermal therapeutic systems as known to one of ordinary skill in the art.

After a sufficient amount of the drug or agent has been delivered through the body surface, or after a predetermined application time has elapsed, the current source 20 is disengaged and the transdermal delivery device can be removed from the body surface.

Changes may be made in the construction and the operation of the various components, elements and assemblies described herein or in the steps or the sequence of steps of the methods described herein without departing from the spirit and scope of the invention as defined in the following claims.

What is claimed is:

1. A transdermal agent delivery device, comprising:
    an active agent reservoir comprising:
        a matrix comprising an ionized hydrophobic polymer matrix, wherein the matrix is substantially free of a hydrophilic component,
        a saturated aqueous solution/suspension of an active agent, and
        a surfactant for maintaining the saturated aqueous solution/suspension of the active agent emulsified or dispersed within the matrix; and
    wherein the active agent reservoir is connectable to a source of electrical power.

2. The device of claim 1 wherein the hydrophobic polymer is a silicone polymer.

3. The device of claim 1 wherein the active agent reservoir further comprises a pressure sensitive adhesive incorporated therein for adhering the reservoir to the body surface.

4. The device of claim 1 further comprising a pressure sensitive adhesive layer for adhering the device to the body surface.

5. The device of claim 1 wherein the active agent reservoir further comprises an ionizing agent.

6. A transdermal agent delivery device, comprising:
    an active agent reservoir comprising:
        a matrix comprising a hydrophobic polymer, wherein the matrix is substantially free of a hydrophilic component, a saturated aqueous solution/suspension of an active agent, a biocompatible pressure sensitive adhesive, and a surfactant for maintaining the saturated aqueous solution/suspension of the active agent emulsified or dispersed within the matrix; and wherein the active agent reservoir is connectable to a source of electrical power.

7. The device of claim 6 wherein the hydrophobic polymer is a silicone polymer.

8. The device of claim 6 wherein the active agent reservoir further comprises an ionizing agent.

9. A transdermal agent delivery device, comprising:

an active agent reservoir comprising:

an ionized silicone polymer matrix, wherein the matrix is substantially free of a hydrophilic component, a saturated aqueous solution/suspension of an active agent, and a surfactant for maintaining the saturated aqueous solution/suspension of the active agent emulsified or dispersed within the matrix; and wherein the active agent reservoir is connectable to a source of electrical power.

10. The device of claim 9 wherein the active agent reservoir further comprises a pressure sensitive adhesive incorporated therein for adhering the reservoir to the body surface.

11. The device of claim 9 further comprising a pressure sensitive adhesive layer for adhering the device to the body surface.

12. The device of claim 9 wherein the active agent reservoir further comprises an ionizing agent.

13. A method for iontophoretically administering an active agent through a body surface, comprising:

applying to the body surface a transdermal delivery device comprising:

an active agent reservoir comprising:

an ionized hydrophobic polymer matrix, wherein the matrix is substantially free of a hydrophilic component, a saturated aqueous solution of an active agent, and a surfactant for maintaining the saturated aqueous solution/suspension of the active agent emulsified or dispersed within the matrix; and generating an electric field across the active agent reservoir and across the body surface such that the active agent is transported to the body surface.

14. The method of claim 13 wherein the hydrophobic polymer of the active agent reservoir is a silicone polymer.

15. The method of claim 13 wherein the step of applying the device to the body surface comprises adhesively adhering the device to the body surface via a biocompatible pressure sensitive adhesive.

16. The method of claim 15 wherein the adhesive is disposed within the active agent reservoir.

17. The method of claim 15 wherein the adhesive comprises an external layer disposed upon the agent reservoir.

\* \* \* \* \*